United States Patent [19]

Mayer et al.

[11] Patent Number: 5,354,904
[45] Date of Patent: Oct. 11, 1994

[54] SULFONAMIDES DERIVED FROM 1-HYDROXY-6-AMINONAPHTHALENE-3-SULFONIC ACID (J ACID)

[75] Inventors: Udo Mayer, Frankenthal; Ulrike Schloesser, Mannheim, both of Fed. Rep. of Germany

[73] Assignee: BASF Aktiengesellschaft, Ludwigshafen, Fed. Rep. of Germany

[21] Appl. No.: 957,781

[22] Filed: Oct. 8, 1992

[30] Foreign Application Priority Data

Oct. 10, 1991 [DE] Fed. Rep. of Germany ....... 4133514

[51] Int. Cl.$^5$ ............... C07D 211/06; C07C 311/39
[52] U.S. Cl. .................... 564/86; 534/872; 534/878; 544/165; 544/398; 544/400; 546/206; 546/232; 546/233; 548/203; 548/204; 548/235; 548/247; 548/335.5; 548/338.1; 548/375.1; 548/566; 548/517; 548/568
[58] Field of Search ............... 564/88, 86, 89; 534/872, 878; 546/206

[56] References Cited

U.S. PATENT DOCUMENTS

| | | | |
|---|---|---|---|
| 3,338,880 | 8/1967 | Favre et al. | 260/156 |
| 3,514,439 | 5/1970 | Wehrli et al. | 260/147 |
| 4,001,204 | 1/1977 | Krutak, Sr. et al. | 260/152 |

FOREIGN PATENT DOCUMENTS 0651917 4/1951 United Kingdom .

OTHER PUBLICATIONS

J. Bredt, et al., Journal fur Praktische Chemie, vol. 101, 1921, pp. 54–57.
A. T. Peters, Dyes and Pigments, vol. 14, 1990, pp. 35–48. "The Synthesis of Disperse and Cationic Dyes from Acid Dye Structures".

*Primary Examiner*—Peter O'Sullivan
*Attorney, Agent, or Firm*—Oblon, Spivak, McClelland, Maier & Neustadt

[57] ABSTRACT

The sulfonamides have the formula

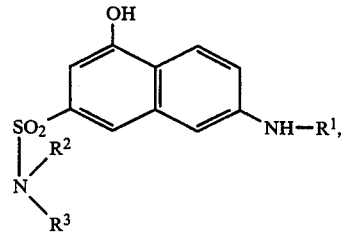

where
$R^1$ is $C_1$–$C_{13}$-lkyl, substituted or unsubstituted phenyl, $C_1$–$C_8$-alkanoyl or substituted or unsubstituted benzoyl, and
$R^2$ and $R^3$ are each independently of one another substituted or unsubstituted $C_1$–$C_{13}$-alkyl, substituted or unsubstituted $C_5$–$C_7$-cycloalkyl or substituted or unsubstituted piperidinyt, or $R^2$ may also be hydrogen.

3 Claims, No Drawings

SULFONAMIDES DERIVED FROM 1-HYDROXY-6-AMINONAPHTHALENE-3-SULFONIC ACID (J ACID)

The present invention concerns novel sulfonamides of the formula I

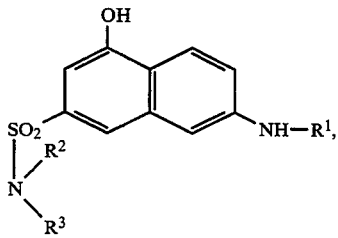

where $R^1$ is $C_1-C_{13}$-alkyl, substituted or unsubstituted phenyl, $C_1-C_8$-alkanoyl or substituted or unsubstituted benzoyl, and $R^2$ and $R^3$ are identical or different and each is independently of the other $C_1-C_{13}$-alkyl, optionally interrupted by from 1 to 4 imino or $C_1-C_4$-alkylimino groups and which can be substituted by amino, by a 5- or 6-membered heterocyclic radical with a nitrogen atom and optionally a further hetero atom selected from the group consisting of nitrogen, oxygen and sulfur, or by substituted or unsubstituted $C_5-C_7$-cycloalkyl, substituted or unsubstituted $C_5-C_7$-cycloalkyl or unsubstituted or methyl-substituted piperidinyl, or $R^2$ may also be hydrogen.

The N-phenylsulfonamide of N-acetyl- or N-benzoyl-J acid is known from J. Prakt. Chem. 101 (1921), 55.

It is an ebbeeL of the present invention to provide novel sulfonamides derived from 1-hydroxy-6-aminonaphthalene-3-sulfcnic acid (J acid). The novel sulfonamides shall be advantageously useful for preparing dyes.

We have found that this object is achieved by the sulfonarnides of the formula I defined at the beginning.

Any alkyl appearing in the abovementioned formula can be not only straight-chain but also branched.

Any substituted phenyl appearing in the above-mentioned formula may have as substituents for example $C_1-C_4$-alkyl, $C_1-C_4$-alkoxy or halogen, in particular chlorine or bromine. The phenyl groups in general have from 1 to 3 substituents.

Any substituted $C_5-C_7$-cycloalkyl appearing in the abovementioned formula may have as substituents for example $C_1-C_4$-alkyl or $C_1-C_4$-aminoalkyl. The cycloalkyl groups in general have from 1 to 3 alkyl groups and/or one aminoalkyl group.

Any methyl-substituted piperidinyl appearing in the abovementioned formula has in general from 1 to 4 methyl groups, preference being given to substituted 4-piperidinyl.

Any $C_1-C_{13}$-alkyl $R^2$ or $R^3$ substituted by a 5-, 6- or 7-membered heterocyclic radical with a nitrogen atom and optionally a further hetero atom selected from the group consisting of nitrogen, oxygen and sulfur may have as substituents saturated or aromatic radicals, such as pyrrolidinyl, piperidinyl, morpholinyl, piperazinyl, N-($C_1-C_4$-alkyl)piperazinyl, pyrrolyl, pyrazolyl, imidazoyl, oxazolyl, isooxazolyl, thiazolyl or isothiazolyl.

Any substituted alkyl appearing in the above-mentioned formula will in general be monosubstituted or disubstituted.

$R^1$, $R^2$ and $R^3$ are each for example methyl, ethyl, propyl, isopropyl, butyl, isobutyl, sec-butyl, tertbutyl, pentyl, isopentyl, neopentyl, tert-pentyl, hexyl, 2-methylpentyl, heptyl, octyl, 2-ethylhexyl, isooctyl, nonyl, isononyl, decyl, isodecyl, undecyl, dodecyl, tridecyl, 3,5,5,7-tetramethylnonyl, isotridecyl (the above designations isooctyl, isononyl, isodecyl and isotridecyl are trivial names derived from the oxo process alcohols - cf. Ullmanns Encyklopädie der technischen Chemie, 4th edition, volume 7, pages 215-217, and also volume 11, pages 4.35 and 436), benzyl or 1- or 2-phenylethyl. Further examples of $R^1$ are phenyl, 2-, 3- or 4-methylphenyl, 2,4-dimethylphenyl, 2-, 3- or 4-methoxyphenyl, 2,4-dimetnoxyphenyl, 2-, 3- or 4-chlorophenyl and 2,4-dichlorophenyl.

$R^1$ may also be for example formyl, acetyl, propionyl, butyryl, isobutyryl, pentanoyl, hexanoyl, heptanoyl, octanoyl, 2-ethylhexanoyl, benzoyl, 2-, 3- or 4-methylbenzoyl, 2,4-dimethylbenzoyl, 2-, 3- or 4-methoxybenzoyl, 2,4-dimethoxybenzoyl, 2-, 3- or 4-chlorobenzoyl or 2,4-dichlorobenzoyl.

$R^2$ and $R^3$ may each also be for example 2-aminoethyl, 2- or 3-aminopropyl, 2- or 4-aminobutyl, 5-aminopentyl, 6-aminohexyl, 7-aminoheptyl, 8-aminooctyl, 3-aza-3-methylbutyl, 4-aza-4-methylpentyl, 3-aza-3-ethylpentyl, 4-aza-4-ethylhexyl, 5-a/nino-3-azapentyl, 6-amino-3-azahexyl, 6-amino-4-azahexyl, 7-amino-4-azaheptyl, 8-amino-3,6-diazaocnyi, 3-aminoprop-2-yl, 8-amino-4-(2-aminoethyl)octyl, 2-(pyrrolidin-1-yl)ethyl, 2- or 3-(pyrrolidin-1-yl)propyl, 2-(piperidin-1-yl)ethyi, 2- or 3-(piperidin-1-yl)propyi, 2-(morpholin-4-yl)ethyl, 2- or 3-(morpholin-4-yl)propyi, 2-(piperazin-1-yl)ethyl, 2- or 3-(piperazin-1-yl)propyl, 2-(4-methylpiperazin-1-yl)ethyl, 2- or 3-(4-methylpiperazin-1-yl)propyl, 2-(imidazol-1-yl)ethyl, 2- or 3-(imidazol-1-yl)propyl, cyclopentyl, cyclohexyl, cycloheptyl, 3-aminomethyl-3,5,5-trimethylcyclohexyl or 2,2,6,6-tetramethylpiperidin-4-yl.

Preference is given to sulfonamides of the formula I where $R^1$ is $C_1-C_4$-alkyl, phenyl, $C_2-C_4$-alkanoyl or benzoyl.

Preference is further given to sulfonamides of the formula I where $R^2$ is hydrogen and $R^3$ is $C_1-C_{13}$-alkyl with at least one quaternizable nitrogen atom.

For the purposes of the present invention, $C_1-C_{13}$-alkyl with at least one quaternizable nitrogen atom is in particular $C_1-C_{13}$-alkyl interrupted by 1 or 2 imino or $C_1-C_4$-alkylimino groups and/or substituted by amino or a 5- or 6-membered saturated or aromatic heterocyclic radical with one or two nitrogen atoms.

Particular preference is given to sulfonamides of the formula I where $R^1$ is acetyl.

The novel sulfonamides of the formula I can be obtained in a conventional manner. For example, a sulfonyl halide of the formula II

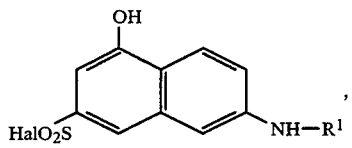

where Hal is halogen, in particular chlorine, and $R^1$ is as defined above, can be reacted with an amine of the formula III

where $R^2$ and $R^3$ are each as defined above.

The sulfonyl halides of the formula II can be prepared for example by the methods described in Dyes and Pigments 14 (1990), 35–48.

The sulfonamides of the formula I according to the present invention are useful intermediates preparing dyes.

The Examples which follow will further illustrate the invention.

EXAMPLE 1

6.5 g of N-acetyl-J acid chloride were added to 30 g of octylamine and the mixture was stirred at room temperature for 60 hours. The resulting solution was then stirred twice with 200 ml of petroleum ether. After the solvent had been decanted off, water and glacial acetic acid were added to the remaining oil to crystallize out 7 g (81 %) of sulfonamide of the formula

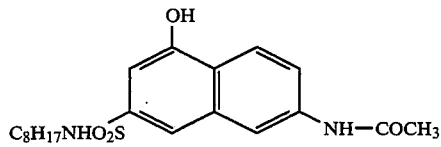

The same method gives the compounds listed below in the table as Examples 6, 7 and 8.

EXAMPLE 2

7 g of N-acetyi-J acid chloride were added to 30 g of 1,2-diaminopropane at 20° C. and the mixture was stirred at room temperaLure for 60 hours and at 80° C. for a further 2 hours.

The resulting oil of the formula

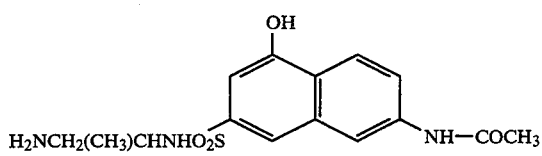

can be used directly in further reactions.

The same method gives the compounds listed below in the table as Examples 3, 4, 5, 9 and 10.

TABLE

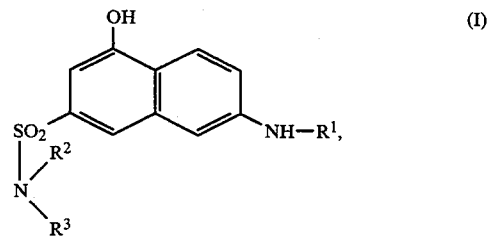

| Ex. no. | $R^1$ | $R^2$ | $R^3$ | $R_f$-Wert *) |
|---|---|---|---|---|
| 1 | $CH_3CO$ | H | $n\text{-}C_8H_{17}$ | 0,51 a) |
| 2 | $CH_3CO$ | H | $CH(CH_3)CH_2NH_2$ | 0,39 b) |
| 3 | $CH_3CO$ | H | $C_3H_6NH_2$ | 0,29 b) |
| 4 | $CH_3CO$ | H | $C_2H_4NH_2$ | 0,32 b) |
| 5 | $CH_3CO$ | H | (2,2,6,6-tetramethylpiperidin-4-yl) | 0,35 b) |
| 6 | $CH_3CO$ | $n\text{-}C_4H_9$ | $n\text{-}C_4H_9$ | 0,45 a) |
| 7 | $C_6H_5CO$ | $n\text{-}C_4H_9$ | $n\text{-}C_4H_9$ | 0,51 a) |
| 8 | $C_6H_5CO$ | H | $n\text{-}C_8H_{17}$ | 0,35 a) |
| 9 | $C_6H_5CO$ | H | $C_2H_4NH_2$ | 0,21 b) |
| 10 | $CH_3$ | H | $C_3H_6NH_2$ | 0,50 b) |

*) The $R_f$-values were determined on TLC aluminum foils (from Merck, Darmstadt) coated with silica gel 60 $F_{254}$ in a thickness of 0.2 mm. The mobile phase used was in case a) 3:1:1 v/v/v toluene/ethyl acetate/acetic acid, and in case b) 4:1:3 v/v/v ethyl acetate/acetic acid/ethanol.

We claim:
1. A sulfonamide of the formula I

$$\text{(I)}$$

where
- $R^1$ is $C_1$–$C_{13}$-alkyl, substituted or unsubstituted phenyl, $C_1$–$C_8$-alkanoyl or substituted or unsubstituted benzoyl, and
- $R^2$ and $R^3$ are identical or different and each is independently of the other $C_1$–$C_{13}$-alkyl, optionally interrupted by from 1 to 4 imino or $C_1$–$C_4$-alkylimino groups and which may optionally be substituted by amino, by a 5- or 6-membered heterocyclic radical with a nitrogen atom and optionally a further hereto atom selected from the group consisting of nitrogen, oxygen and sulfur, or by substituted or unsubstituted $C_5$–$C_7$-cycloalkyl or unsubstituted or methyl-substituted piperidinyl, or $R^2$ may also be hydrogen.

2. A sulfonamide as claimed in claim 1, wherein $R^1$ is $C_1$–$C_4$-alkyl, phenyl, $C_2$–$C_4$-alkanoyl or benzoyl.

3. A sulfonamide as claimed in claim 1, wherein $R^2$ is hydrogen and $R^3$ is $C_1$–$C_3$-alkyl with at least one quaternizable nitrogen atom.

* * * * *